United States Patent
Cragun et al.

(10) Patent No.: US 8,677,282 B2
(45) Date of Patent: Mar. 18, 2014

(54) MULTI-FINGER TOUCH ADAPTATIONS FOR MEDICAL IMAGING SYSTEMS

(75) Inventors: Brian J. Cragun, Rochester, MN (US); Michael J. Fork, Gibsonburg, OH (US)

(73) Assignee: International Business Machines Corporation, Armonk, NY (US)

( * ) Notice: Subject to any disclaimer, the term of this patent is extended or adjusted under 35 U.S.C. 154(b) by 542 days.

(21) Appl. No.: 12/465,273

(22) Filed: May 13, 2009

(65) Prior Publication Data
US 2010/0293500 A1 Nov. 18, 2010

(51) Int. Cl.
G06F 3/048 (2013.01)
G06F 3/033 (2013.01)

(52) U.S. Cl.
USPC .......................... 715/863; 715/784

(58) Field of Classification Search
USPC .................................. 715/784, 863
See application file for complete search history.

(56) References Cited

U.S. PATENT DOCUMENTS

| | | | |
|---|---|---|---|
| 6,323,846 B1 * | 11/2001 | Westerman et al. | 345/173 |
| 6,958,749 B1 | 10/2005 | Matsushita et al. | |
| 2008/0168402 A1 | 7/2008 | Blumenberg | |
| 2009/0138800 A1 * | 5/2009 | Anderson et al. | 715/702 |

FOREIGN PATENT DOCUMENTS

EP 1942401 A1 9/2008

OTHER PUBLICATIONS http://en.wikipedia.org/wiki/Multi-touch, "Multi-touch", pp. 1-2, printed Mar. 17, 2008.
http://www.ted.com/index.php/talks/view/id/65, "Talks Jeff Han: Unveiling the genius of multi-touch interface design", pp. 1-3, printed Mar. 17, 2008.
http://cs.nyu.edu/~jhan/ftirtouch/, "Multi-Touch Interaction Research", pp. 1-4, printed Mar. 17, 2008.

* cited by examiner

*Primary Examiner* — Andrea Leggett
(74) *Attorney, Agent, or Firm* — Patterson & Sheridan LLP (57) ABSTRACT

Systems, methods and articles of manufacture are disclosed for presenting image slices in a windowing environment based on multi-touch user input, the image slices generated by an imaging system. A series of image slices may be provided that represent a view of an object. A gesture may be defined based on at least a count of fingers represented in multi-touch user input. Further, the defined gesture may be associated with a corresponding action for manipulating an image slice. Multi-touch user input may be received. Upon determining that the received multi-touch user input includes the defined gesture, the corresponding action may be performed on an image slice of the series to generate a resultant image slice. The resultant image slice may be output via an output device.

24 Claims, 8 Drawing Sheets

MULTI-FINGER TOUCH ADAPTATIONS FOR MEDICAL IMAGING SYSTEMS

BACKGROUND OF THE INVENTION

1. Field of the Invention

The field of the invention relates to presenting images. More specifically, the field of the invention relates to presenting images in a windowing environment based on multi-touch user input, the images generated by a medical imaging system.

2. Description of the Related Art

Windowing environments are common in the medical field. Such environments facilitate medical analysis via displaying medical images side by side on a large screen. Medical imaging systems may include scanners (such as computed tomography (CT) scanners and magnetic resonance imaging (MRI) scanners) which provide views inside a body. These views may be organized into a stack or series of visual "slices" (i.e., image slices). Trained individuals analyze the stack of image slices by scrolling back and forth in the stack. In addition, many image manipulations aid in the analysis of the image slices, such as changing the brightness and contrast, combining slices in various ways (e.g., maximum intensity projection (MIP), and automatic edge detection and object identification.

SUMMARY OF THE INVENTION

One embodiment of the invention includes a method for presenting image slices in a windowing environment based on multi-touch user input, the image slices generated by an imaging system, the method comprising configuring one or more processors to perform an operation. The operation may generally include providing a series of image slices representing a view of an object; defining a gesture based on at least a count of fingers represented in multi-touch user input; associating the defined gesture with a corresponding action for manipulating an image slice; receiving multi-touch user input; upon determining that the received multi-touch user input includes the defined gesture, performing the corresponding action on an image slice of the series to generate a resultant image slice; and outputting the resultant image slice via an output device.

Another embodiment of the invention includes a computer readable storage medium containing a program which, when executed, performs an operation for presenting image slices in a windowing environment based on multi-touch user input, the image slices generated by an imaging system. The operation may generally include providing a series of image slices representing a view of an object; defining a gesture based on at least a count of fingers represented in multi-touch user input; associating the defined gesture with a corresponding action for manipulating an image slice; receiving multi-touch user input; upon determining that the received multi-touch user input includes the defined gesture, performing the corresponding action on an image slice of the series to generate a resultant image slice; and outputting the resultant image slice via an output device.

Still another embodiment of the invention includes a system having a processor and a memory containing a program, which when executed by the processor is configured to perform an operation for presenting image slices in a windowing environment based on multi-touch user input, the image slices generated by an imaging system. The operation may generally include providing a series of image slices representing a view of an object; defining a gesture based on at least a count of fingers represented in multi-touch user input; associating the defined gesture with a corresponding action for manipulating an image slice; receiving multi-touch user input; upon determining that the received multi-touch user input includes the defined gesture, performing the corresponding action on an image slice of the series to generate a resultant image slice; and outputting the resultant image slice via an output device.

BRIEF DESCRIPTION OF THE DRAWINGS

So that the manner in which the above recited features, advantages and objects of the present invention are attained and can be understood in detail, a more particular description of the invention, briefly summarized above, may be had by reference to the embodiments thereof which are illustrated in the appended drawings.

It is to be noted, however, that the appended drawings illustrate only typical embodiments of this invention and are therefore not to be considered limiting of its scope, for the invention may admit to other equally effective embodiments.

DETAILED DESCRIPTION OF THE PREFERRED EMBODIMENTS

Embodiments of the present invention generally provide for the presentation of image slices in a windowing environment based on multi-touch user input. The image slices may be generated by a medical imaging system, for example. Image selection and manipulation are facilitated by multi-touch user input.

In the following, reference is made to embodiments of the invention. However, it should be understood that the invention is not limited to specific described embodiments. Instead, any combination of the following features and elements, whether related to different embodiments or not, is contemplated to implement and practice the invention. Furthermore, although embodiments of the invention may achieve advantages over other possible solutions and/or over the prior art, whether or not a particular advantage is achieved by a given embodiment is not limiting of the invention. Thus, the following aspects, features, embodiments and advantages are merely illustrative and are not considered elements or limitations of the appended claims except where explicitly recited in a claim(s). Likewise, reference to "the invention" shall not be construed as a generalization of any inventive subject matter disclosed herein and shall not be considered to be an element or limitation of the appended claims except where explicitly recited in a claim(s).

One embodiment of the invention is implemented as a program product for use with a computer system. The program(s) of the program product defines functions of the embodiments (including the methods described herein) and can be contained on a variety of computer-readable storage media. Illustrative computer-readable storage media include, but are not limited to: (i) non-writable storage media (e.g., read-only memory devices within a computer such as CD-ROM disks readable by a CD-ROM drive) on which information is permanently stored; (ii) writable storage media (e.g., floppy disks within a diskette drive or hard-disk drive) on which alterable information is stored. Such computer-readable storage media, when carrying computer-readable instructions that direct the functions of the present invention, are embodiments of the present invention. Other media include communications media through which information is conveyed to a computer, such as through a computer or telephone network, including wireless communications networks. The latter embodiment specifically includes transmitting information to/from the Internet and other networks. Such communications media, when carrying computer-readable instructions that direct the functions of the present invention, are embodiments of the present invention. Broadly, computer-readable storage media and communications media may be referred to herein as computer-readable media.

In general, the routines executed to implement the embodiments of the invention, may be part of an operating system or a specific application, component, program, module, object, or sequence of instructions. The computer program of the present invention typically is comprised of a multitude of instructions that will be translated by the native computer into a machine-readable format and hence executable instructions. Also, programs are comprised of variables and data structures that either reside locally to the program or are found in memory or on storage devices. In addition, various programs described hereinafter may be identified based upon the application for which they are implemented in a specific embodiment of the invention. However, it should be appreciated that any particular program nomenclature that follows is used merely for convenience, and thus the invention should not be limited to use solely in any specific application identified and/or implied by such nomenclature.

Figure 1:
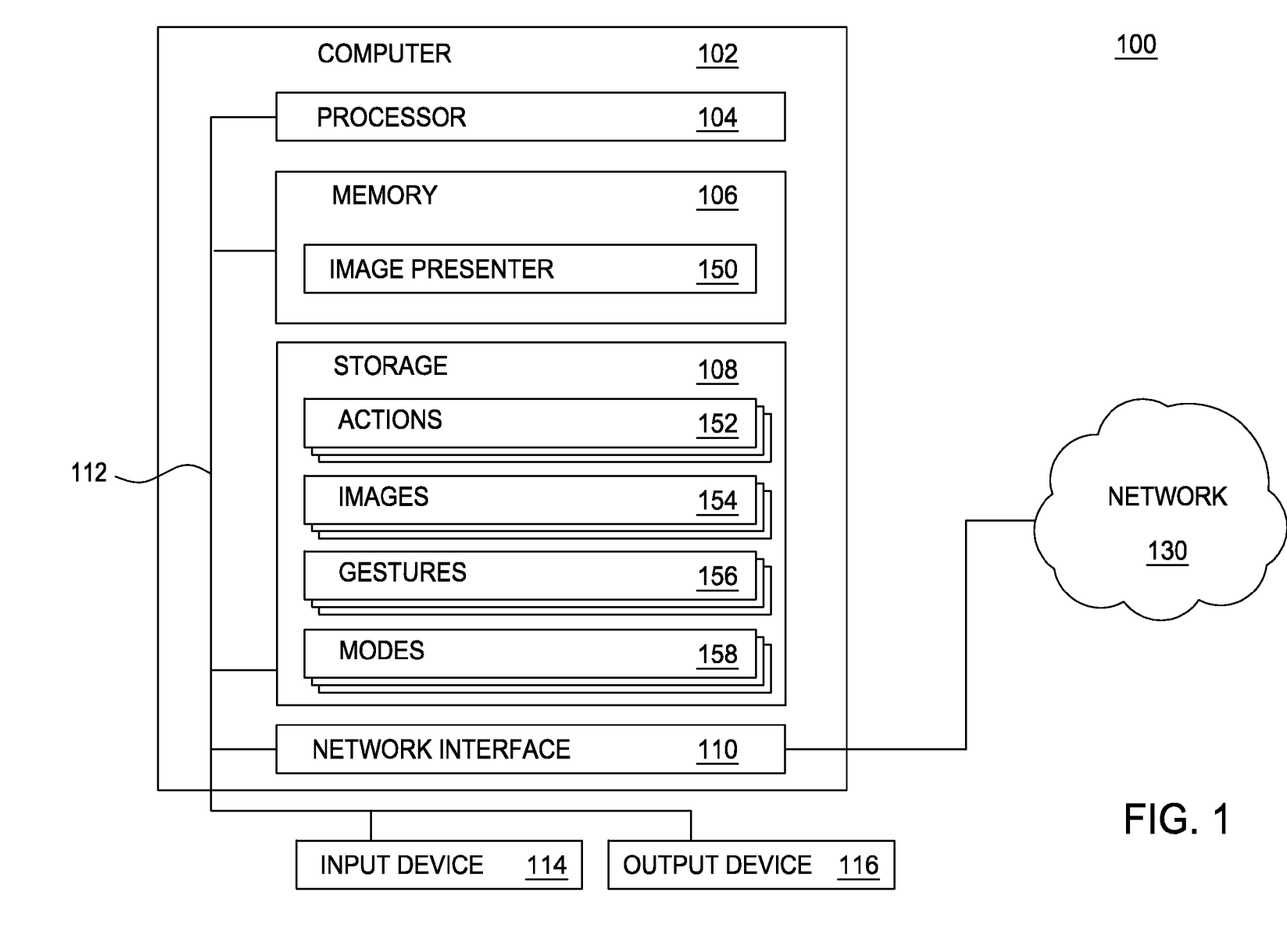
FIG. 1 is a block diagram illustrating a system for presenting images in a windowing environment based on multi-touch input, the images generated by a medical imaging system, according to one embodiment of the invention.

FIG. 1 is a block diagram illustrating a system 100 for presenting images in a multi-touch windowing environment, the images generated by a medical imaging system, according to one embodiment of the invention. The networked system 100 includes a computer 102. The computer 102 may be connected to other computers via a network 130. In general, the network 130 may be a telecommunications network and/or a wide area network (WAN). In a particular embodiment, the network 130 is the Internet.

The computer 102 generally includes a processor 104 connected via a bus 112 to a memory 106, a network interface device 110, a storage 108, an input device 114, and an output device 116. The computer 102 is generally under the control of an operating system (not shown). Examples of operating systems include UNIX, versions of the Microsoft Windows® operating system, and distributions of the Linux® operating system. (Note: Linux is at trademark of Linus Torvalds in the United States and other countries.) More generally, any operating system supporting the functions disclosed herein may be used.

The memory 106 may be a random access memory. While the memory 106 is shown as a single entity, it should be understood that the memory 106 may in fact comprise a plurality of modules, and that the memory 106 may exist at multiple levels, from high speed registers and caches to lower speed but larger DRAM chips.

The network interface device 110 may be any entry/exit device configured to allow network communications between the computer 102 and the server 132 via the network 130. For example, the network interface device 110 may be a network adapter or other network interface card (NIC).

The storage 108 may be a hard disk drive storage device. Although the storage 108 is shown as a single unit, the storage 108 may be a combination of fixed and/or removable storage devices, such as fixed disc drives, floppy disc drives, tape drives, removable memory cards, or optical storage. The storage 108 may also include network-attached storage. The memory 106 and the storage 108 may be part of one virtual address space spanning multiple primary and secondary storage devices.

The input device 114 may be any device for providing multi-touch input to the computer 102. A multi-touch input device may include a touch screen or touchpad (and any accompanying software) that recognizes multiple simultaneous touch points (e.g., from a human hand) on the touch screen or on the touchpad. In contrast, a conventional touch screen or touchpad only recognizes a single touch point and thus cannot provide multi-touch input to the computer 102.

The output device 116 may be any device for providing output to a user of the computer 102. For example, the output device 116 may be any conventional display screen or set of speakers, along with their respective interface cards, i.e., video cards and sound cards (not shown). Although shown separately from the input device 114, the output device 116 and input device 114 may be combined. For example, a display screen with an integrated touch screen (or touch pad) or a display with an integrated keyboard may be used.

As shown, the memory 106 of the computer 102 includes an image presenter 150. Further, the storage 108 of the computer 102 includes actions 152, images 154, gestures 156, and modes 158. FIGS. 2 through 6 and associated descriptions detail the structure and operation of the image presenter 150 running on the computer 102.

Figure 7A:
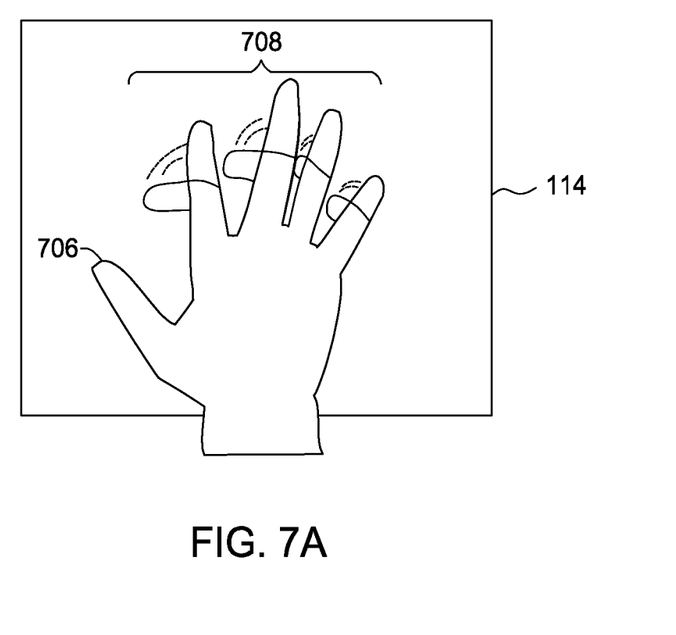
FIGS. 7A-7C illustrate selecting scrolling modes using multi-touch input, according to one embodiment of the invention.
Figure 7B:
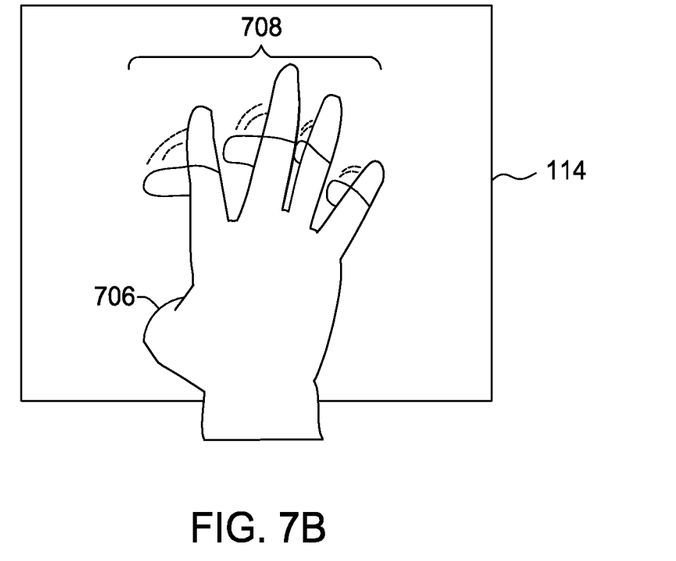
Figure 7C:
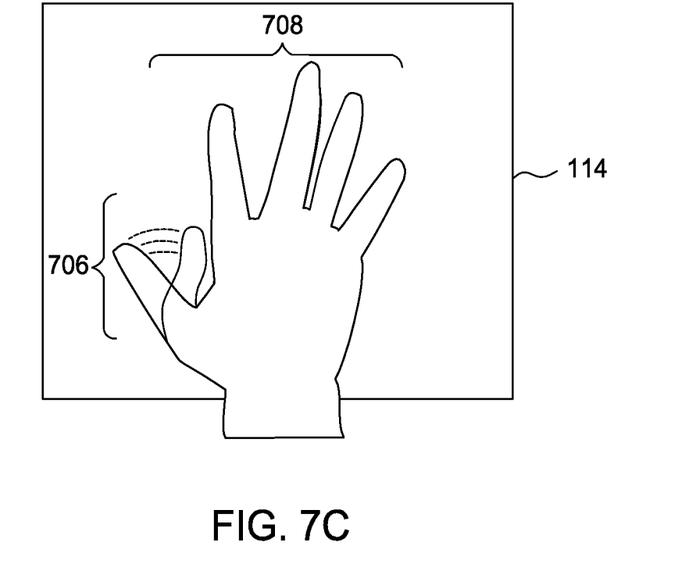

FIGS. 7A-7C illustrate selecting scrolling modes using multi-touch input, according to one embodiment of the invention. In one embodiment, a user may select from a predefined set of scrolling modes. For example, a predefined set of scrolling modes may include (i) a "fine" scrolling mode for scrolling an image five pixels at a time and (ii) a "coarse" scrolling mode for scrolling an image ten pixels at a time.

A user may implicitly select a scrolling mode, according to one embodiment. For example, a user may scroll an image finely using a single finger (i.e., a user may implicitly select the fine scrolling mode by scrolling using a single finger on the input device 114). Alternatively, a user may scroll an image coarsely using a three fingers (i.e., a user may implicitly select the coarse scrolling mode by scrolling an image using three fingers on the input device 114).

Further, a user may select a scrolling mode using a thumb position on the input device 114, according to one embodiment. Each scrolling mode of the predefined set of scrolling modes may be associated with a predefined thumb position. The predefined thumb position may be a position relative to other fingers on the input device 114. For example, a thumb position under the fingers may be associated with the coarse scrolling mode. Further, a thumb position not under the fingers may be associated with the fine scrolling mode.

FIG. 7A illustrates a user scrolling with fingers 708 on the input device 114. In this particular example, the user's thumb 706 is positioned away from (i.e., not under) the fingers 708. That is, the image presenter 150 may select the fine scrolling mode based on the user's thumb position being away from the fingers 708. The user may then scroll an image finely using the fingers 708.

Like FIG. 7A, FIG. 7B illustrates a user scrolling with fingers 708 on the input device 114. In this particular example, however, the user's thumb 706 is positioned under the fingers 708. In this case, the image presenter 150 may select the coarse scrolling mode based on the user's thumb position being under the fingers 708. The user may then scroll an image coarsely using the fingers 708.

Further, a user may select a scrolling mode using a thumb gesture on the input device 114, according to one embodiment. For example, the user may toggle through a plurality of scrolling modes using a single thumb gesture (e.g., a thumb swipe) on the input device 114. Selecting scrolling modes via a gesture is further described below in conjunction with Table VIII.

FIG. 7C illustrates a user scrolling with fingers 708 on the input device 114. In this particular example, the user is performing a thumb swipe on the input device 114. The image presenter 150 may toggle the scrolling mode based on the thumb swipe. For example, suppose the current (i.e., active) scrolling mode is the fine scrolling mode. The user may scroll an image finely using the fingers 708 on the input device 114. The user may also swipe the thumb 706 to toggle the scrolling mode. That is, the image presenter 150 may change the scrolling mode from the fine scrolling mode to the coarse scrolling mode in response to a thumb swipe. Subsequently, the user may scroll the image coarsely using the fingers 708 on the input device 114. Selecting scrolling modes via a toggle is further described below in conjunction with Table IX.

Figure 2:
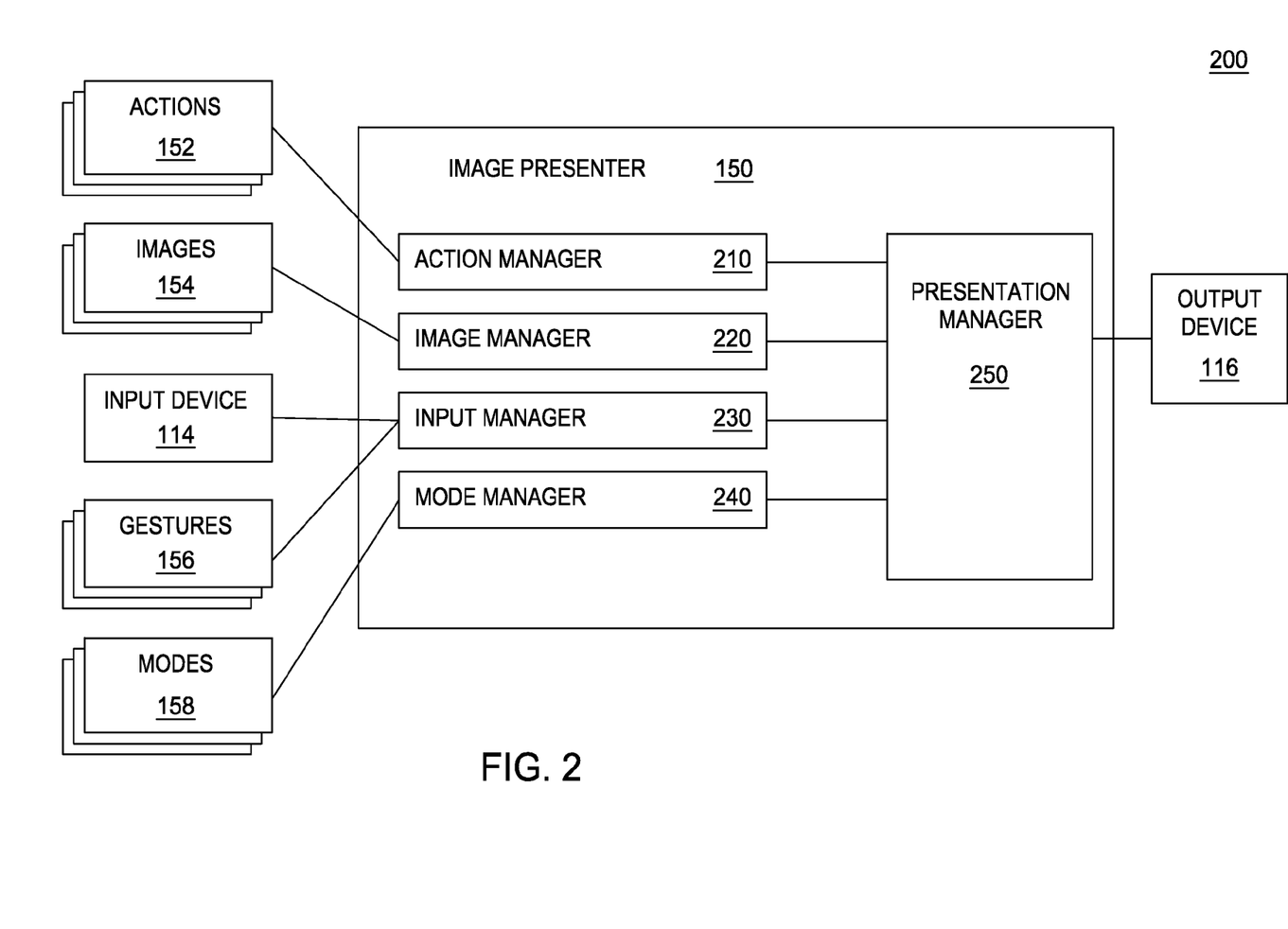
FIG. 2 is a block diagram illustrating a functional view of an image presenter, according to one embodiment of the invention.

FIG. 2 is a block diagram illustrating a functional view 200 of the image presenter 150 of FIG. 1, according to one embodiment of the invention. As shown, the image presenter 150 includes an action manager 210, an image manager 220, an input manager 230, a mode manager 240, and a presentation manager 250.

The image presenter may receive multi-touch user input for performing an action on the image slices. The image presenter may identify a number (or count) of fingers represented in the received multi-touch user input. Further, the image presenter may perform an action on (i.e., manipulate) the image slices based on the identified number of fingers to generate resultant image slices. The identified number of fingers may also determine an image slice on which to perform the action. Further, an action may be defined by one or more attributes. The image presenter may modify an attribute of an action based on the received multi-touch user input. The image presenter may also define modes (i.e., modes of image manipulation) that provide default values for attributes. Further, the image presenter may output the resultant image slices to a user via an output device. Taken together, a user may use multi-touch input to perform an action on an image slice without having to separately or individually select one or more of an image slice, an action, an attribute, and a mode.

In one embodiment, the image manager selects one or more images on which to perform an action from a plurality of images based on input received from the input manager. The plurality of images may be one or more series of image "slices." For example, each series may represent a view of a human body, the view being provided by scanners of a medical imaging system. Examples of scanners include computed tomography (CT) scanners, magnetic resonance imaging (MRI) scanners, etc. Further, each image may be an image slice from the one or more series of image slices.

More generally, the "body" or "subject" represented by the images may be any variety of living or non-living material. Thus, images of a part of a human body are merely illustrative, and are not intended to be limiting of the invention. For example, the images may be of any living organism, such as an animal. Further, while embodiments are described herein with reference to images generated by scanners of a medical imaging system, those skilled in the art will recognize that embodiments of the invention may be adapted to support other imaging applications. For example, the plurality of images may include planar slice views of a 3D depiction of a mechanical system, such as an automobile or a truck engine. As another example, the plurality of images may include planar slice views of a 3D depiction of an architectural system, such as a 3D rendering of a building.

In one embodiment, the action manager 210 defines a plurality of actions 152 which may be performed on one or more of the plurality of images 154. The plurality of actions 152 may be any action for manipulating output of images in a windowing environment via the output device 116. That is, the action manager 210 may manipulate a copy of the images residing in the memory 106 rather than the images located in the storage 108, according to one embodiment. Table I shows illustrative actions:

TABLE I

Action examples

Increase/decrease brightness of an image
Increase/decrease contrast of an image
Increase/decrease zoom of an image
Scroll image up/down/left/right
Move to a next/previous image
Combine two images
Perform edge detection and/or object identification in an image
Link two images As shown, the actions 152 may include adjusting brightness of an image, adjusting contrast of an image, adjusting zoom of an image, scrolling an image, flipping to another image, combining two images, performing edge detection, performing object identification, linking two images (i.e., for a later action to be performed simultaneously on linked images), etc. Adjusting brightness of an image may include increasing or decreasing brightness of the image. Adjusting contrast of an image may include increasing or decreasing contrast of the image. Further, a user may scroll an image in a direction. The direction may include up, down, left, right, or any direction determined from user input received via the input device 114. The user may also move to a next or previous image of a series of images (e.g., a series of image slices of a view representing of a human body, the view being provided by a scanner of a medical imaging system). In addition, the user may combine two images via any technique such as maximum intensity projection (MIP), subtraction, etc. That is, a user may create a third image based on (i.e., by combining) a first image and second image. For example, the third image may highlight differences between the first image and the second image. A user may also perform edge detection and/or object identification in an image. For example, a user may detect edges or identify objects (e.g., tissue, bone, etc.) in an image slice.

In one embodiment, the input manager 230 receives user input via the input device 114. Further, the input manager 230 defines a plurality of gestures 156. Each gesture 156 represents a discrete input from the user via the input device 114. That is, the user inputs a gesture 156 on a multi-touch input device 114. Further, each gesture 156 may include any number of fingers (from one or both hands) detectable by the input device 114. A finger refers to any digit on a human hand (e.g., thumb, index finger, middle finger, ring finger, little finger).

A gesture may be defined by a spatial positioning of fingers. For example, a first gesture may be defined as any three fingers positioned on the multi-touch input device 114. Further, a gesture may be defined by a relative positioning of fingers. For example, a second gesture may be defined as any three fingers positioned on the multi-touch device, such that each finger is spaced at least two inches apart from the other fingers on the multi-touch input device 114. Further still, a gesture may be defined by temporal positioning (i.e., movement) of fingers. For example, a third gesture may be defined as any three fingers swiping upwards on the multi-touch input device 114. Table II shows illustrative gestures:

TABLE II

Gesture examples

A number of fingers tapping simultaneously
A number of fingers tapping in a specific sequence
A number of fingers fixed on the input device
A number of fingers fixed in a predefined relative configuration on the input device
A number of fingers swiping in a direction (right/left, up/down, up-left, etc.)
A number of fingers twisting in an orientation (clockwise, counterclockwise, etc.)
A number of fingers making a grasping motion
A number of fingers making a sprawling motion
Any combination of the above gestures As shown, the gestures 156 may include a number of fingers tapping simultaneously (e.g., three fingers tapping simultaneously), a number of fingers tapping in a specific sequence (e.g., three fingers tapping in succession such as thumb, index finger and middle finger), a number of fingers fixed on the input device (e.g., three fingers fixed on the input device), a number of fingers fixed in a predefined relative configuration on the input device (e.g., three fingers fixed at positions spaced at least two inches apart from one another on the input device), a number of fingers swiping in a direction (e.g., for a predefined distance, such as a quarter-inch), a number of fingers twisting in an orientation (e.g., clockwise, counterclockwise), a number of fingers making a grasping motion, a number of fingers making a sprawling motion, or any combination thereof.

The input manager 230 may also associate each gesture 156 with a corresponding action 152, according to one embodiment. Table III shows illustrative gesture associations:

TABLE III

Gesture association example - action

| Gesture | Associated action |
|---|---|
| Two fingers swiping up | Increase brightness |
| Two fingers swiping down | Decrease brightness |
| Three fingers swiping up | Increase contrast |
| Three fingers swiping down | Decrease contrast |

In this specific example, the input manager 230 associates a gesture 156 of "two fingers swiping up" with an action 152 for increasing brightness. That is, a user may swipe two fingers upwards on the input device 114 to increase brightness of an image slice 154. Further, the input manager 230 associates a gesture 156 of "two fingers swiping down" with an action 152 for decreasing brightness. That is, a user may swipe two fingers downwards on the input device 114 to decrease brightness of the image slice 154. Further, the input manager 230 associates a gesture 156 of "three fingers swiping up" with an action 152 for increasing contrast. That is, a user may swipe three fingers upwards on the input device 114 to increase contrast of the image slice 154. Further, the input manager 230 associates a gesture 156 of "three fingers swiping down" with an action 152 for decreasing contrast. That is, a user may swipe three fingers downwards on the input device 114 to decrease contrast. Taken together, the user may manipulate output of an image slice 154 by swiping two fingers for adjusting brightness of the image slice 154 and by swiping three fingers for adjusting contrast of the image slice 154.

The input manager 230 may also associate a gesture with a target image on which the associated action is to be performed. Table IV shows illustrative gesture associations that include target images:

TABLE IV

Gesture association example - target image

| Gesture | Associated action and target image |
|---|---|
| One finger swiping up | Scroll first displayed image upwards |
| One finger swiping down | Scroll first displayed image downwards |
| Two fingers swiping up | Scroll second displayed image upwards |
| Two fingers swiping down | Scroll second displayed image downwards |
| Three fingers swiping up | Scroll third displayed image upwards |
| Three fingers swiping down | Scroll third displayed image downwards |
| Four fingers swiping up | Scroll all displayed images upwards |
| Four fingers swiping down | Scroll all displayed images downwards |

In this specific example, the input manager 230 associates a gesture 156 of "swiping up" with an action 152 of "scrolling an image upwards." Further, the input manager 230 associates a gesture 156 of "swiping down" with an action 152 of "scrolling an image downwards." In addition, the input manager 230 may associate each gesture 156 with a target image based on a number of fingers of user input received via the input device 114. That is, suppose the image presenter 250 outputs three image slices side by side via the output device 116. In this specific example, one finger selects a first displayed image; two fingers select a second displayed image; three fingers select a third displayed image; and four fingers select all displayed images (i.e., three images in this case). For example, a user may scroll the first displayed image upwards by swiping a single finger up via the input device 114. If the user swipes two fingers up via the input device 114, the image presenter 250 scrolls the second displayed image upwards (instead of scrolling the first displayed image upwards).

In one embodiment, each action 152 may include one or more attributes (or parameters). Performance of an action may be defined by one or more attributes. That is, an attribute may specify a manner in which an associated action is to be performed. Table V shows an illustrative attribute for an action:

TABLE V

Attribute example

| | |
|---|---|
| Attribute name: | Precision |
| Associated action: | Scrolling |
| Attribute effect: | Determines how finely or coarsely to scroll |

For example, a "scrolling" action 152 may include an associated "precision" attribute. The precision attribute determines how finely or coarsely to scroll an image slice 154. For example, scrolling finely may be defined as scrolling five pixels at a time, while scrolling coarsely may be defined as scrolling ten pixels at a time. In one embodiment, the action manager 210 may adjust an attribute based on user input. Table VI shows an illustrative attribute that is based on user input:

TABLE VI

Scrolling example - precision is based on user input

| Action | Gesture |
| --- | --- |
| Scroll finely | Swipe two fingers slowly in a desired direction |
| Scroll coarsely | Swipe two fingers quickly in a desired direction |

As shown, a user may swipe two fingers slowly in a desired direction to scroll an image slice finely in the desired direction. Further, a user may swipe two fingers quickly in a desired direction to scroll an image slice coarsely in the desired direction. Taken together, a rate of movement associated with a gesture affects the precision attribute of the scrolling action.

In one embodiment, the mode manager 240 defines a plurality of modes 158. Each mode 158 specifies one or more default attributes for an action 152. Table VII shows illustrative modes:

TABLE VII

Mode examples

For scrolling

Fine scrolling mode
Coarse scrolling mode
For moving to a next/previous image slice Fine flipping mode (e.g., 1 image slice at a time)
Coarse flipping mode (e.g., 3 image slices at a time)
For combining two image slices Subtraction mode
Maximum intensity projection (MIP) mode
For performing edge detection Searched-based algorithm
Zero crossing-based algorithm As shown, the mode manager 240 defines two modes 158 for scrolling: a fine scrolling mode and a coarse scrolling mode. Further, the mode manager 240 defines two modes 158 for moving to a next or previous image: a fine flipping mode (e.g., 1 image slice at a time) or a coarse flipping mode (e.g., 3 image slices at a time). The mode manager 240 also defines two modes 158 for combining image slices: a subtraction mode and a maximum intensity projection (MIP) mode. For example, a user may use subtraction mode to combine two images to generate a new image. In subtraction mode, each pixel of the new image may be the difference of corresponding pixels of the two images (e.g., a pixel of the first image minus a corresponding pixel of the second image). Further, a user may also use maximum intensity projection to combine two or more images to generate a new image. In maximum intensity projection mode, each pixel of the new image may be the maximum (i.e., brightest) value of corresponding pixels of the two or more images. Other modes for combining image slices are broadly contemplated.

In addition, the mode manager 240 defines two modes for performing edge detection: using a search-based algorithm or a zero-crossing based algorithm. A search-based algorithm computes a measure of edge strength using a first-order derivative of pixel intensity and searches for local directional maxima of the computed edge strength. A zero-crossing based algorithm uses a second-order derivative of pixel intensity (i.e., rate of change of pixel intensity) and searches for zero-crossings (i.e., points where a function crosses an axis). Other algorithms for performing edge detection are broadly contemplated.

The mode manager 240 specifies a default attribute (such as "coarse") for an action (such as "scrolling"). Although embodiments herein are described with reference to a mode manager 240 that defines modes in pairs, those skilled in the art will recognize that any number of modes may be supported by embodiments of the invention. For example, the mode manager 240 may define a "Medium scrolling" mode for Table VII.

The mode manager 240 may also associate each mode 158 with a gesture 156. That is, a user may input a gesture 156 to select an associated mode 158. Table VIII shows illustrative modes with associated gestures:

TABLE VIII

Scrolling mode example - thumb position

| Mode | Gesture |
| --- | --- |
| Fine scrolling mode | Thumb position under other fingers |
| Coarse scrolling mode | Thumb position not under other fingers |

In this specific example, the mode manager 240 associates a fine scrolling mode with a gesture that includes a thumb positioned under other fingers. For example, a user may finely scroll an image slice 154 down by swiping fingers downward with a thumb at a position under the fingers. Further, the mode manager 240 associates a coarse scrolling mode with a gesture that includes a thumb positioned other than under other fingers. For example, a user may coarsely scroll an image slice 154 down by swiping fingers downward with a thumb at a position other than under the fingers. Taken together, the user may modify the precision attribute of the scrolling action using a thumb position on the input device 114.

In addition, the mode manager 240 may also associate a plurality of modes 158 with a single gesture, thereby creating (for two modes) a mode toggle or (for three or more modes) a mode cycle. That is, a user may toggle between two modes using a mode toggle, and cycle between three or more modes using a mode cycle. Table IX shows an illustrative mode toggle:

TABLE IX

Scrolling mode example - thumb swipe

| Mode | Gesture |
| --- | --- |
| Fine scrolling mode | Toggle - Thumb swipe (Default) |
| Coarse scrolling mode | Toggle - Thumb swipe |

In this specific example, the mode manager 240 associates both the fine scrolling mode and the coarse scrolling mode with a gesture of a thumb swipe, thereby creating a toggle for the scrolling action. That is, a thumb swipe need not be used for scrolling, but may merely be used for specifying a scrolling mode (e.g., fine or coarse). A user may then scroll (e.g., finely or coarsely) using fingers. Further, the mode manager 240 specifies the fine scrolling mode as a default mode. For example, a user may finely scroll an image slice 154 up based on a default mode by swiping fingers upward. If a user performs a thumb swipe on the input device 114, the mode manager 240 "toggles" the scrolling mode, thereby selecting the coarse scrolling mode. At this point, a user may coarsely scroll an image slice 154 up by swiping fingers upward. If a user performs a second thumb swipe on the input device 114, the mode manager 240 toggles the scroll mode again, thereby re-selecting (i.e., reverting to) the fine scrolling mode. At this point, a user may once again finely scroll an image slice 154 up by swiping fingers upward.

In one embodiment, the presentation manager 250 outputs an image slice 154 to a user via the output device 116. The image slice 154 may include an image slice that results from performing an action 152 on an image slice 154. For example, the presentation manager 250 may output an image slice 154 that results from performing any of the actions of Table II. The presentation manager 250 is further discussed below in conjunction with FIG. 3.

Figure 3:
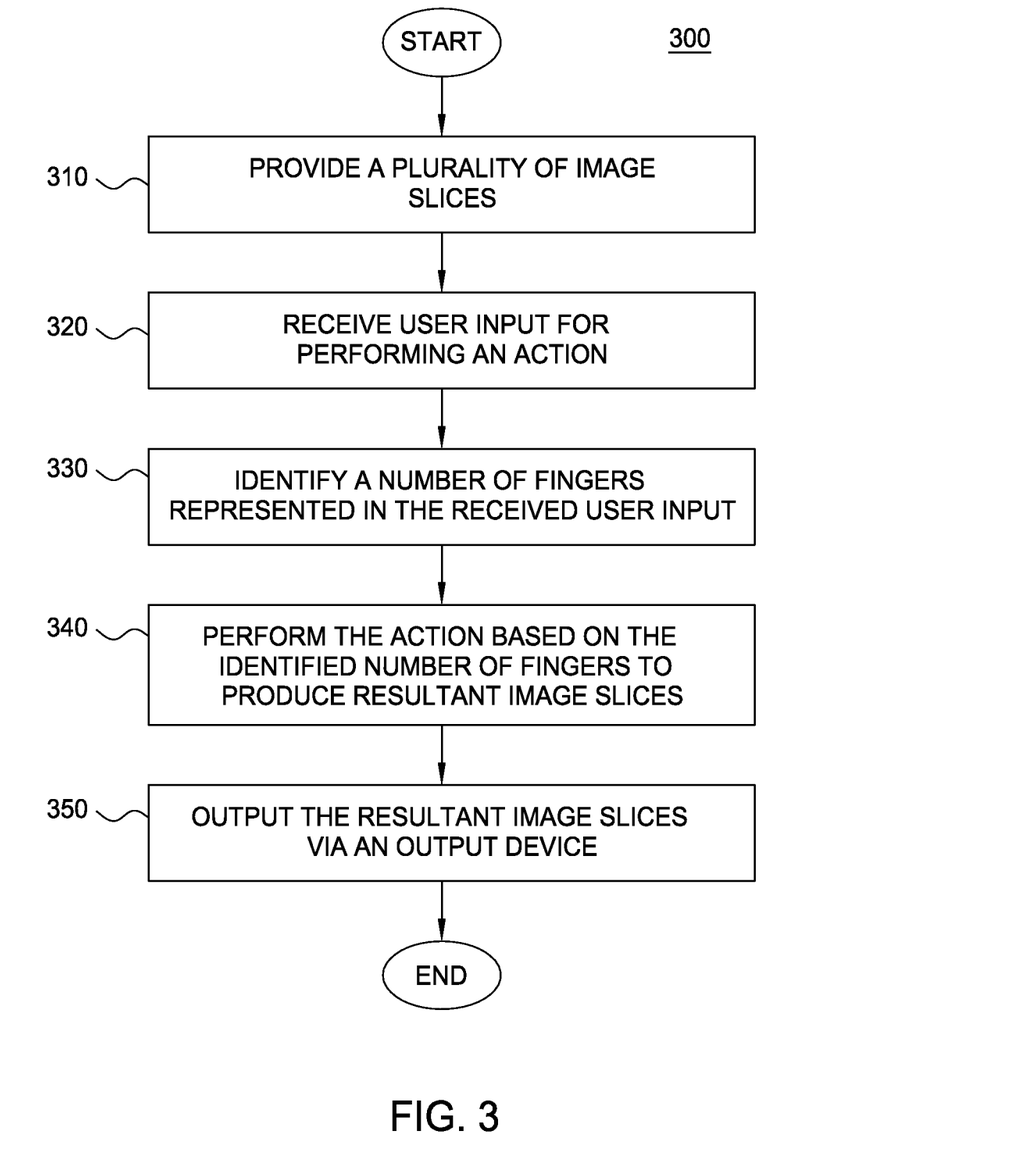
FIG. 3 is a flowchart depicting a method for presenting images in a windowing environment based on multi-touch input, the images generated by a medical imaging system, according to one embodiment of the invention.

FIG. 3 is a flowchart depicting a method 300 for presenting images 154 in a windowing environment based on multi-touch input, the images 154 generated by a medical imaging system, according to one embodiment of the invention. The method 300 may be performed by the image presenter 150 of FIG. 1. The steps of the method 300 are described in conjunction with the action example of Table I and with the gesture association examples of Tables III and IV.

As shown, the method 300 begins at step 310, where the image manager 220 provides a plurality of image slices 154. For example, the image manager 220 may provide image slices from an MRI scan of a human body. At step 320, the image manager 220 may receive user input for performing an action 152 on one or more image slices from the plurality of image slices 154. For example, the image manager 220 may receive user input for performing an action from Table I, III, or IV.

At step 330, the input manager 230 provides a number of fingers of the received user input. In one embodiment, the input manager 230 may receive a number of fingers from the input device 114. Alternatively, the input manager 230 may also receive the number of fingers from device drivers, an operating system, a window manager, or an application executing on the computer 102. In another embodiment, the input manager 230 may also determine the number of fingers based on the user input received from the input device 114. For example, absolute coordinates of five touch points may be mapped to five fingers according to an anatomy of a human hand.

At step 340, the action manager 210 performs an action 152 based on the number of fingers to generate resultant image slices. For example, the action manager 210 may perform an associated action from Table III or Table IV to generate resultant image slices. In one embodiment, the image slices 154 are modified by performing the associated action, and the resultant image slices are stored in the storage 108. In another embodiment, only a copy of the image slices 154 existing in the memory 106 may be modified by performing the associated action. That is, the associated action may be performed on image slices 154 merely for output purposes; the image slices 154 in storage 108 are not modified. At step 350, the presentation manager 250 outputs the resultant image slices to the user via the output device 116. After step 350, the method 300 terminates.

Figure 4:
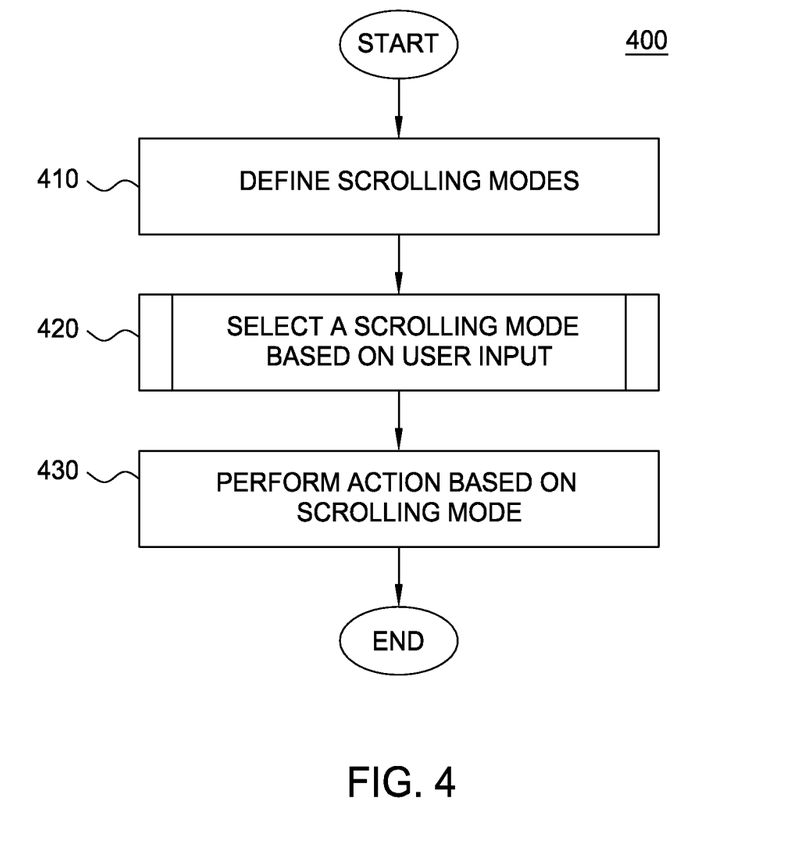
FIG. 4 is a flowchart depicting a method for selecting a scrolling mode, according to one embodiment of the invention.

FIG. 4 is a flowchart depicting a method 400 for selecting a scrolling mode, according to one embodiment of the invention. The method 400 may be performed by the image presenter 150 of FIG. 1. The steps of the method 400 are described in conjunction with the mode example of Table VII and with the scrolling mode examples of Tables VIII and IX. Further, those skilled in the art will recognize that the method 400 is exemplary and is not intended to be limiting of the invention. For example, selecting modes 158 other than scrolling modes (such as any mode 158 of Table VII) is broadly contemplated.

As shown, the method 400 begins at step 410, where the mode manager 240 defines a plurality of modes 158. In this particular example, the mode manager 240 defines a plurality of scrolling modes, such as the scrolling modes of Table VII. Further, the mode manager 240 may associate each mode 158 with user input. For example the mode manager 240 may associate each mode 158 with a gesture 156 of Table VIII or IX.

At step 420, the mode manager 240 selects a scrolling mode based on user input. For example, the mode manager 240 receives a gesture 156 (provided by the input manager 230) and selects a mode 158 of Table VIII or IX corresponding to the received gesture 156. Step 420 is further described below in conjunction with FIGS. 5-6. At step 430, the action manager 210 performs an action based on user input and the selected scrolling mode. For example, if the coarse scrolling mode of FIG. IX is selected, the action manager 210 may scroll an image slice 154 coarsely based on user input (e.g., a gesture of Table IV). After step 430, the method 400 terminates.

Figure 5:
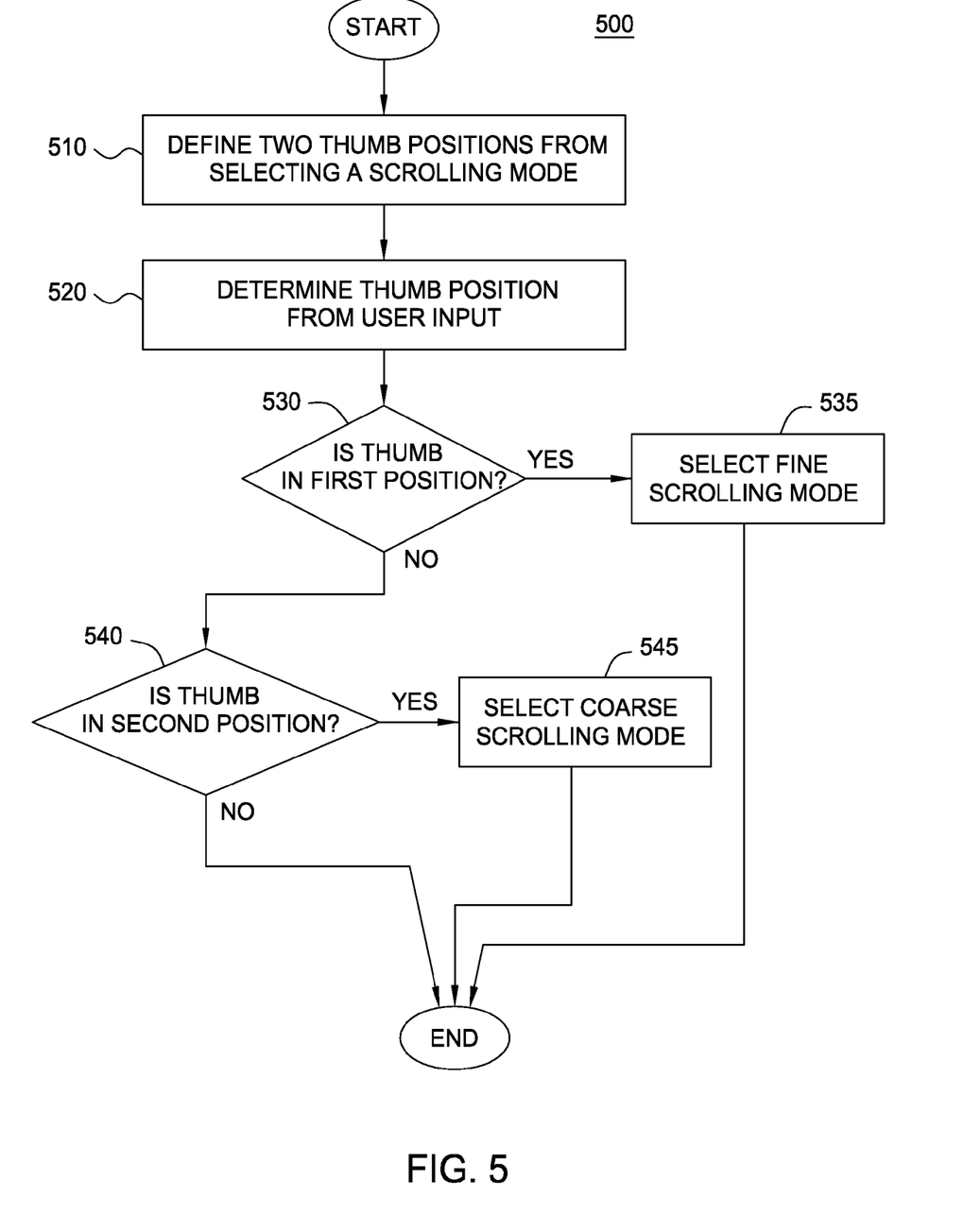
FIG. 5 is a flowchart depicting a method for selecting a scrolling mode based on a thumb position, according to one embodiment of the invention.

FIG. 5 is a flowchart depicting a method 500 for selecting a scrolling mode based on a thumb position, according to one embodiment of the invention. The method 500 may be performed by the image presenter 150 of FIG. 1. The steps of method 500 correspond to step 420 of FIG. 4 and are described in conjunction with the scrolling mode example of Table VIII. Further, those skilled in the art will recognize that the method 500 is exemplary and is not intended to be limiting of the invention. For example, selecting modes 158 other than scrolling modes (such as any mode 158 of Table VII) is broadly contemplated. Further, selecting a mode 158 based on user input other than a thumb position is broadly contemplated.

As shown, the method 500 begins at step 510, where the mode manager 240 defines two thumb positions for selecting a scrolling mode. For example, the mode manager 240 defines two thumb positions of Table VIII. At step 520, the input manager 230 determines a thumb position from user input. For example, the input manager 230 may determine a thumb position that is under other fingers of the user input. At step 530, the mode manager 240 determines whether the thumb position matches a first defined thumb position (e.g., the first gesture of Table VIII). If so, the method 500 proceeds to step 535, where the mode manager 240 selects a scrolling mode corresponding to the first defined thumb position. For example, if the mode manager 240 detects a thumb position that is under other fingers, the mode manager 240 may select a fine scrolling mode, according to Table VIII. After step 535, the method 500 terminates.

If the thumb position does not match a first defined thumb position, the method 500 proceeds to step 540, where the mode manager 240 determines whether the thumb position matches a second defined thumb position (e.g., the second gesture of Table VIII). For example, if the mode manager 240 detects a thumb position that is not under other fingers, the mode manager 240 may select a coarse scrolling mode, according to Table VIII. After step 535 or step 540, the method 500 terminates.

Figure 6:
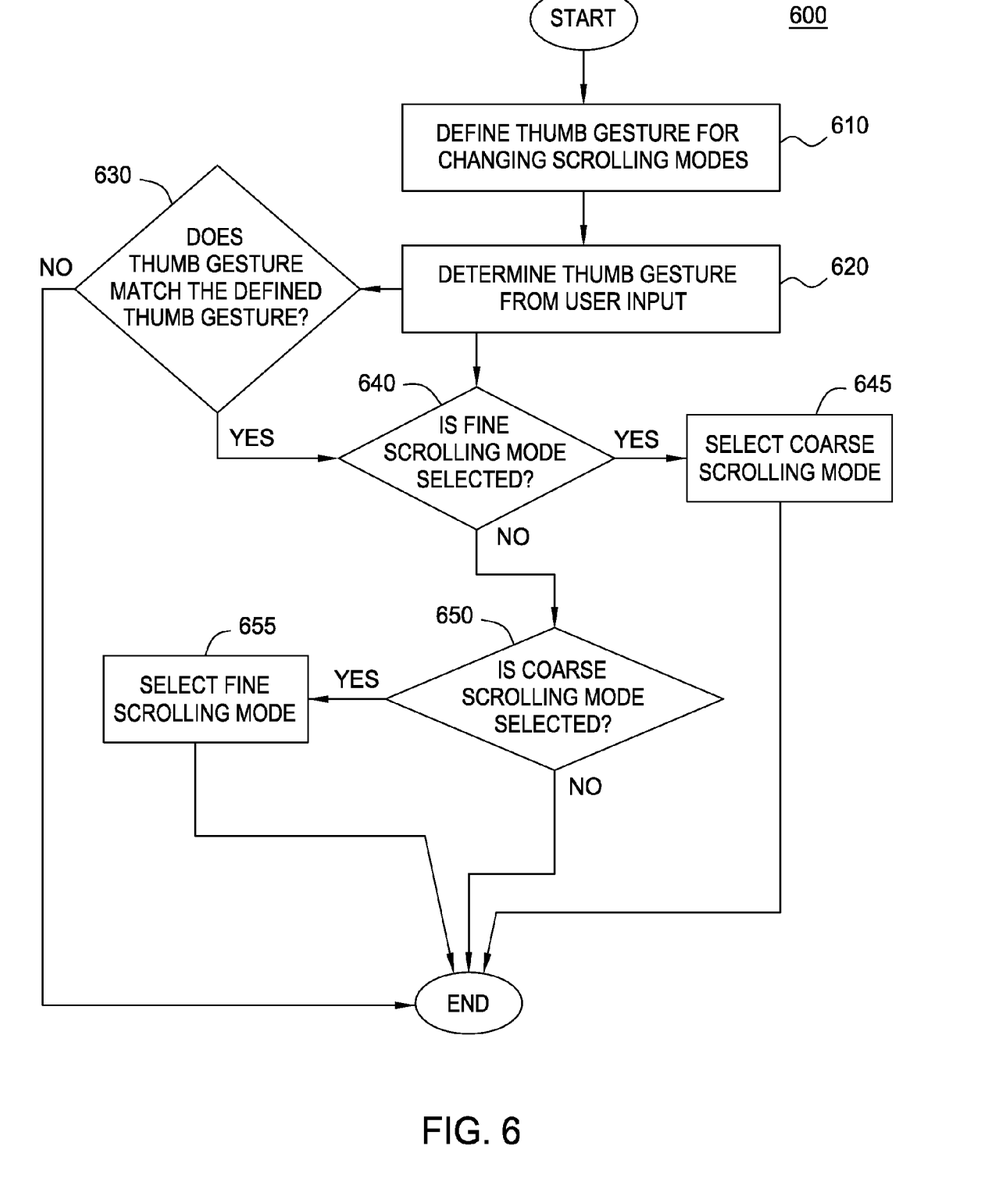
FIG. 6 is a flowchart depicting a method for selecting a scrolling mode based on a thumb gesture, according to one embodiment of the invention.

FIG. 6 is a flowchart depicting a method 600 for selecting a scrolling mode based on a thumb gesture, according to one embodiment of the invention. The method 600 may be performed by the image presenter 150 of FIG. 1. The steps of method 600 correspond to step 420 of FIG. 4 and are described in conjunction with the scrolling mode example of Table IX. Further, those skilled in the art will recognize that the method 600 is exemplary and is not intended to be limiting of the invention. For example, selecting modes 158 other than scrolling modes (such as any mode 158 of Table VII) is broadly contemplated. Selecting a mode 158 based on user input other than a thumb gesture is also broadly contemplated.

As shown, the method 600 begins at step 610, where the mode manager 240 defines a thumb gesture for changing scrolling modes. For example, the mode manager 240 defines a thumb gesture of Table IX. At step 620, the input manager 230 detects a thumb gesture from user input. For example, the input manager 230 may detect a thumb swipe from the user input. At step 630, the mode manager 240 determines whether the thumb gesture matches the defined thumb gesture (e.g., the gesture of Table IX). If not, the method 600 terminates.

However, if the mode manager 240 determines that the thumb gesture matches the defined thumb gesture, the method 600 proceeds to step 640, where the mode manager 240 determines whether a fine scrolling mode is currently selected. If so, the method 600 proceeds to step 645, where the mode manager 240 selects a coarse scrolling mode, thereby "toggling" scrolling modes (e.g., of Table IX). After step 645, the method 600 terminates.

If the mode manager 240 determines that a fine scrolling mode is not currently selected, the method 600 proceeds to step 650, where the mode manager 240 determines whether a coarse scrolling mode is currently selected. If so, the method 600 proceeds to step 655, where the mode manager 240 selects a fine scrolling mode, thereby toggling scrolling modes (e.g., of Table IX). After step 655 or step 650, the method 600 terminates.

Of course, the embodiments described herein are intended to be illustrative and not limiting of the invention, and other embodiments are broadly contemplated. Those skilled in the art will recognize, for example, that embodiments of the invention may be adapted to support other images (i.e., images other than image slices), actions, gestures, attributes, and modes. Further, multi-touch input from more than one hand may be supported by embodiments of the invention. For example, the image presenter may receive a gesture of three fingers with a right hand on a first image and three fingers with a left hand on a second image. In response to the gesture, the image presenter may perform an associated action of linking the first image and the second image for combined scrolling. In addition, sequences of gestures may be supported by embodiments of the invention. For example, the image presenter may receive three sequential gestures for linking three images for combined scrolling. The three sequential gestures may include three fingers on a first image, followed by three fingers on a second image, followed by three fingers on a third image (regardless of a right hand or a left hand).

Advantageously, embodiments of the invention present image slices in a windowing environment based on multi-touch user input, the image slices generated by an imaging system. In one embodiment, an image presenter may receive multi-touch user input for performing an action on the image slices. The image presenter may identify a number of fingers of the received multi-touch user input. Further, the image presenter may perform an action on the image slices based on the identified number of fingers to generate resultant image slices. The identified number of fingers may determine an image slice on which to perform the action. Further, behavior of an action may be defined by one or more attributes. The image presenter may modify an attribute based on the received multi-touch user input. Moreover, the image presenter may define modes that provide default values for attributes. The image presenter may also output the resultant image slices to a user via an output device. Taken together, a user may use multi-touch input to perform an action on an image slice without having to separately or individually select one or more of an image slice, an action, an attribute, and a mode. Further, a user may more efficiently navigate through image slices of a stack.

While the foregoing is directed to embodiments of the present invention, other and further embodiments of the invention may be devised without departing from the basic scope thereof, and the scope thereof is determined by the claims that follow.

What is claimed is:

1. A computer-implemented method for presenting image slices in a windowing environment by using multi-touch user input to identify an image viewing command and a mode thereof, the image slices generated by an imaging system, the method comprising:
    providing a series of image slices including a first image slice representing a view of an object;
    receiving multi-touch user input including at least one of a stationary digit and a gesture including one or more moving digits;
    programmatically identifying an image viewing command from a plurality of distinct image viewing commands, upon determining that the gesture matches a first predefined gesture of a plurality of distinct predefined gestures, each predefined gesture corresponding to a distinct image viewing command of the plurality of distinct image viewing commands, the image viewing command having a plurality of distinct modes of operation, wherein each mode is identified based on at least one of a distinct stationary digit position and a distinct count of moving digits represented in the gesture, wherein each stationary digit position represents the same digit and is measured relative to the gesture; and
    performing, by operation of one or more computer processors, the identified image viewing command on the first image slice of the series in the identified mode, to generate a graphical output to display responsive to the received multi-touch user input.

2. The computer-implemented method of claim 1, wherein the imaging system is a medical imaging system, and wherein the object comprises part of a living organism.

3. The computer-implemented method of claim 1, wherein the image viewing command is selected from at least one of adjusting brightness of an image slice, adjusting contrast of an image slice, scrolling an image slice, moving from an image slice to a next image slice, combining two image slices, and linking two image slices; and wherein the first predefined gesture specifies a configuration of digits represented in multi-touch user input, wherein the configuration of digits is selected from at least: (i) an absolute position of the digits at a first point in time; (ii) a relative position of the digits at the first point in time; and (iii) movement of the digits.

4. The computer-implemented method of claim 1, wherein the count of moving digits determines an image slice on which to perform the image viewing command.

5. The computer-implemented method of claim 1, wherein the image viewing command is scrolling an image slice, and wherein the count of moving digits determines how finely to scroll the image slice.

6. The computer-implemented method of claim 1, wherein each mode specifies at least one of a desired level of precision of the image viewing command, a desired target set of images for the image viewing command, and a desired target display attribute to be adjusted by the image viewing command;
   wherein the received multi-touch user input includes both the stationary digit and the gesture including the one or more moving digits, wherein the stationary digit position reflects an absolute position at least over a duration of the gesture, wherein each predefined stationary digit position represents an absolute position.

7. The computer-implemented method of claim 6, wherein each image viewing command is programmatically identified based on the gesture and not based on the at least one of the stationary digit position and the count of moving digits, wherein each mode is identified based on the at least one of the stationary digit position and the count of moving digits and not based on the gesture;
   wherein the multi-touch user input is received by an image viewing application, wherein the image viewing application is configured to programmatically identify each image view command selected from the plurality of distinct image viewing commands, the plurality of distinct image viewing commands including display attribute adjustment, image zooming, image scrolling, image swapping, image combination, and edge detection.

8. The computer-implemented method of claim 7, wherein the image viewing application is further configured to:
   perform image scrolling based individually on each scrolling mode of a plurality of scrolling modes, each scrolling mode specifying a distinct level of precision of image scrolling;
   perform image scrolling based individually on each target mode of a plurality of target modes, each scrolling mode specifying a distinct target set of image slices to be scrolled;
   perform image zooming based individually on each zooming mode of a plurality of zooming modes, each zooming mode specifying a distinct level of precision of image zooming; and
   perform image zooming based individually on each target mode of a plurality of target modes, each target mode specifying a distinct target set of image slices for which to perform image zooming.

9. The computer-implemented method of claim 8, wherein the image viewing application is further configured to:
   swap a target set of image slices for output, based individually on a each target mode of a plurality of target modes, each target mode specifying a distinct set of image slices to be swapped; and
   adjust a display attribute of the image viewing application based individually on each attribute mode of a plurality of attribute modes, each attribute mode specifying a distinct attribute selected from image brightness and image contrast.

10. The computer-implemented method of claim 9, wherein the image viewing application is further configured to:
   combine two image slices based individually on each combination mode of a plurality of combination modes, each combination mode specifying a distinct one of subtraction and maximum intensity projection; and
   perform edge detection on a target image slice, based individually on each detection mode of a plurality of detection modes, each detection mode specifying a distinct one of a search-based algorithm and a zero-crossing-based algorithm.

11. The computer-implemented method of claim 10, wherein the image viewing application is further configured to identify each mode based individually on each of the stationary digit position and the count of moving digits;
   wherein each image slice represents a distinct view of the object, wherein each image viewing command behaves distinctly in each mode, wherein the image viewing application is further configured to define two stationary digit positions comprising the first predefined stationary digit position and the second predefined stationary digit position.

12. The computer-implemented method of claim 11, wherein the image viewing application is further configured to:
   programmatically identify the first mode upon determining at least one of: (i) the stationary digit position matches the first predefined stationary digit position and (ii) the count of moving digits matches a first predefined count of moving digits; and
   programmatically identify the second mode upon determining at least one of: (i) the stationary digit position matches the second predefined stationary digit position and (ii) the count of moving digits matches a second predefined count of moving digits, different from the first predefined count of moving digits.

13. The computer-implemented method of claim 12, wherein the image viewing application is further configured to:
   define a second gesture for changing modes; and
   change modes upon detecting an occurrence of the second gesture for changing modes;
   wherein the plurality of distinct predefined gestures include a predefined gesture for each configuration of digits represented in multi-touch user input, of: (i) an absolute position of the digits at a first point in time; (ii) a relative position of the digits at the first point in time; and (iii) movement of the digits;
   wherein the first predefined stationary digit position is determined as being under a palm of a hand inputting the gesture, wherein the second predefined stationary digit position is determined as not being under the palm of the hand inputting the gesture.

14. The computer-implemented method of claim 13, wherein the image viewing application is further configured to programmatically identify each image viewing command based on the gesture and not based on the stationary digit position and not based on the count of moving digits, wherein the image viewing application is further configured to:
   identify modes of a first image viewing command, based on the stationary digit position and not based on the count of moving digits and not based on the gesture; and
   identify modes of a second image viewing command different from the first image viewing command, based on the count of moving digits and not based on the stationary digit position and not based on the gesture.

15. A computer readable memory containing a program which, when executed, performs an operation for presenting image slices in a windowing environment by using multi-touch user input to identify an image viewing command and a mode thereof, the image slices generated by an imaging system, the operation comprising:

providing a series of image slices including a first image slice representing a view of an object;

receiving multi-touch user input including at least one of a stationary digit and a gesture including one or more moving digits;

programmatically identifying an image viewing command from a plurality of distinct image viewing commands, upon determining that the gesture matches a first predefined gesture of a plurality of distinct predefined gestures, each predefined gesture corresponding to a distinct image viewing command of the plurality of distinct image viewing commands, the image viewing command having a plurality of distinct modes of operation, wherein each mode is identified based on at least one of a distinct stationary digit position and a distinct count of moving digits represented in the finger gesture, wherein each stationary digit position represents the same digit and is measured relative to the gesture; and performing, by operation of one or more computer processors when executing the program, the identified image viewing command on the first image slice of the series in the identified mode, to generate a graphical output to display responsive to the received multi-touch user input.

16. The computer readable memory of claim 15, wherein the imaging system is a medical imaging system, and wherein the object comprises part of a living organism.

17. The computer readable memory of claim 15, wherein the image viewing command is selected from at least one of adjusting brightness of an image slice, adjusting contrast of an image slice, scrolling an image slice, moving from an image slice to a next image slice, combining two image slices, and linking two image slices; and wherein the first predefined gesture specifies a configuration of digits represented in multi-touch user input, wherein the configuration of digits is selected from at least: (i) an absolute position of the digits at a first point in time; (ii) a relative position of the digits at the first point in time; and (iii) movement of the digits.

18. The computer readable memory of claim 15, wherein the count of moving digits determines an image slice on which to perform the image viewing command.

19. The computer readable memory of claim 15, wherein the image viewing command is scrolling an image slice, and wherein the count of moving digits determines how finely to scroll the image slice.

20. A system, comprising:
a processor; and
a memory containing a program, which when executed by the processor is configured to perform an operation for presenting image slices in a windowing environment by using multi-touch user input to identify an image viewing command and a mode thereof, the image slices generated by an imaging system, the operation comprising:

providing a series of image slices including a first image slice representing a view of an object;

receiving multi-touch user input including at least one of a stationary digit and a gesture including one or more moving digits;

programmatically identifying an image viewing command from a plurality of distinct image viewing commands, upon determining that the finger gesture matches a first predefined gesture of a plurality of distinct predefined gestures, each predefined gesture corresponding to a distinct image viewing command of the plurality of distinct image viewing commands, the image viewing command having a plurality of distinct modes of operation, wherein each mode is identified based on at least one of a distinct stationary digit position and a distinct count of moving digits represented in the finger gesture, wherein each stationary digit position represents the same digit and is measured relative to the gesture; and performing the identified image viewing command on the first image slice of the series in the identified mode, to generate a graphical output to display responsive to the received multi-touch user input.

21. The system of claim 20, wherein the imaging system is a medical imaging system, and wherein the object comprises part of a living organism.

22. The system of claim 20, wherein the image viewing command is selected from at least one of adjusting brightness of an image slice, adjusting contrast of an image slice, scrolling an image slice, moving from an image slice to a next image slice, combining two image slices, and linking two image slices; and wherein the first predefined gesture specifies a configuration of digits represented in multi-touch user input, wherein the configuration of digits is selected from at least: (i) an absolute position of the digits at a first point in time; (ii) a relative position of the digits at the first point in time; and (iii) movement of the digits.

23. The system of claim 20, wherein the count of moving digits determines an image slice on which to perform the image viewing command.

24. The system of claim 20, wherein the image viewing command is scrolling an image slice, and wherein the count of moving digits determines how finely to scroll the image slice.

* * * * *